United States Patent [19]

Koizumi et al.

[11] Patent Number: 4,814,596
[45] Date of Patent: Mar. 21, 1989

[54] DETECTION OF SURFACE PARTICLES BY DUAL SEMICONDUCTOR LASERS HAVING STABLE ILLUMINATION INTENSITIES

[75] Inventors: Mitsuyoshi Koizumi; Yoshimasa Ohshima, both of Yokohama, Japan

[73] Assignee: Hitachi, Ltd., Tokyo, Japan

[21] Appl. No.: 74,858

[22] Filed: Jul. 17, 1987

[30] Foreign Application Priority Data

Jul. 21, 1986 [JP] Japan .................................. 61-169701

[51] Int. Cl.[4] ............................................... G01J 1/32
[52] U.S. Cl. .................................... 250/205; 250/571; 356/401
[58] Field of Search ............... 250/205, 214 C, 214 R, 250/571, 572, 548, 557; 356/400, 401, 430, 445, 446, 447, 448

[56] References Cited

U.S. PATENT DOCUMENTS

| 4,363,962 | 12/1982 | Shida | 250/548 |
| 4,375,067 | 2/1983 | Kitamura | 250/205 |
| 4,418,467 | 12/1983 | Iwai | 356/401 |
| 4,523,089 | 6/1985 | Maeda et al. | 250/205 |
| 4,701,609 | 10/1987 | Koishi et al. | 250/214 C |

Primary Examiner—David C. Nelms
Assistant Examiner—William L. Oen
Attorney, Agent, or Firm—Antonelli, Terry & Wands

[57] ABSTRACT

Disclosed is an apparatus for detecting particles comprising semiconductor laser drive means for performing feedback control of semiconductor lasers, each thereof incorporating a sensor therewith for monitoring laser-output thereof, by using the output of the sensor, means for holding the feedback voltage, illuminating means including a plurality of optical means disposed to oppose each other so that the laser-outputs from the semiconductor lasers are obliquely applied onto a specimen, and detection means for detecting the light scattered from the particles present on the specimen.

5 Claims, 5 Drawing Sheets

DETECTION OF SURFACE PARTICLES BY DUAL SEMICONDUCTOR LASERS HAVING STABLE ILLUMINATION INTENSITIES

BACKGROUND OF THE INVENTION

The relates to an apparatus for detecting particles on a surface of semiconductor LSI wafer, photomask, magnetic bubble wafer, or the like by the use of a semiconductor laser capable of stably keeping the quantity of illumination at a predetermined intensity.

The process for detecting the contaminants or particles on wafers with a circuit pattern attached thereto in the course of manufacture of LSIs is essential for increasing the yield of the LSI products and improving reliability on the products. Automation of such detecting process has been embodied by detection methods employing polarized light illumination like those disclosed in Japanese Laid-open Patent Publication No. 55-149829 and others such as U.S. Pat. No. 4,342,515 (Japanese Laid-open Patent Publication Nos. 54-101390, 55-94145), and Japanese Laid-open Patent Publication No. 56-30630. The principle of such method will be described below with reference to FIGS. 10 to 12.

If it is only arranged to have illuminating light 4 incident on the surface of a wafer 1 at an angle of inclination $\phi$ as shown in FIG. 12, then reflected light 5 and scattered light 6 (FIG. 10) are produced simultaneously from the circuit pattern 2 and particles 3 respectively, and therefore, it is impossible to detect only the particles 3 discriminated from the pattern 2. So that it has been devised to detect the particles 3 by the use of a polarized laser beam.

An S-polarized laser beam 4 is arranged to illuminate a pattern 2 present on the wafer 1 as shown in FIG. 11 (a). Herein, a laser beam 4 whose electrical vector 10 is parallel with the surface of the wafer is defined as illumination by an S-polarized laser. Generally, the irregularity on the surface of the pattern 2 seen microscopically is sufficiently small as compared with the wavelength of the illuminating light and optically smooth, so that the S-polarized light 11 reflected from the pattern 2 is preserved in the reflected light 5. Therefore, if an analyzer 13 cutting the S-polarized light is inserted in the optical path of the reflected light 5, the reflected light 5 is cut off and unable to reach a photoelectric conversion element 7. On the other hand, in the scattered light 6 from the particles 3, there is included a P-polarized light 12 in addition to the S-polarized component as shown in FIG. 11 (b). This is because the surface of the particles 3 is rough, and thereby, scattered light 6 is partially polarized and the P-polarized light 12 is generated. Accordingly, if the P-polarized light 14 transmitted through the analyzer 13 is detected by the photoelectric conversion element 7, then detection of the particles 3 becomes possible.

Now, by employing two lasers 15 emitting laser beams from left and right as shown in FIG. 12, execution of stable detection of particles generating anisotropic scattered light becomes possible.

As the laser 15, the He-Ne laser has hitherto been employed in view of high and stable intensity of laser-output, long life, stable polarization characteristic, etc. However, since the He-Ne laser has a large oscillator body in size, it has been difficult to miniaturize the apparatus for detecting particles by using such a laser beam source.

Thus, because of the use of the He-Ne laser for the laser beam source as described above, there has been a problem in the prior art that miniaturization of the apparatus has not been attainable.

SUMMARY OF THE INVENTION

An object of the present invention is to achieve miniaturization of the apparatus by the use of semiconductor lasers for the laser beam sources and provide apparatus for detecting particles capable of stable detection of particles exist on specimens such as semiconductor LSI wafers, photomasks, magnetic bubble wafers by stabilizing the laser-output of the semiconductor lasers.

In order to achieve the object mentioned above, the apparatus for detecting particles of the present invention comprises semiconductor laser drive circuit for performing feedback control of semiconductor lasers, each thereof incorporating a sensor therewith for monitoring laser-output intensity thereof, by using the output of the sensor, means for holding the feedback voltage, illuminating means arranged with a plurality of optical means disposed to oppose each other so that the laser-outputs from the semiconductor lasers are obliquely applied onto a specimen, and detection means for detecting the light scattered from particles that exist on the specimen. That is, the present invention is characterized first in that semiconductor lasers are used as laser beam sources therein, and secondly, in that the operation of feedback control of the laser-output 16a is performed only at the time just before the particle detection process under the condition of the laser beam from the opposing semiconductor laser 16b not incident into the Laser 16a, and the FEEDBACK VOLTAGE from the sensor 18a is sampled and held, and during the particle detection process the semiconductor laser 16a is driven with the feedback voltage held and the output of the monitoring sensor 18a not used, the operation of feedback control of the Laser 16b is same as that of the Laser 16a, and thereby, the detection of the particles is stably executed.

The time period required for detecting the entire surface of one wafer is several minutes as most. Change in the ambient temperature during such a period of time is neglected, and therefore, the laser-output of the semiconductor laser is maintained stable if the feedback voltage is held unchanged during that detection time. Just before detecting the next wafer, the operation of feedback control of the Laser-outputs is performed again. Thus, the variation in the laser-output of the semiconductor laser due to change in the ambient temperature can be eliminated and the performance to detect the particles can be maintained stable.

DETAILED DESCRIPTION OF THE PREFERRED EMBODIMENT

An embodiment of the present invention will be described below with reference to the accompanying drawings.

Recently, a semiconductor laser 16 has been developed which has higher output power and longer life and has therefore become satisfactorily usable as a laser beam source for an apparatus for detecting particles. In achieving miniaturization of the apparatus for detecting particles, it is useful to employ the semiconductor laser 20 as the laser beam source.

Figure 5:
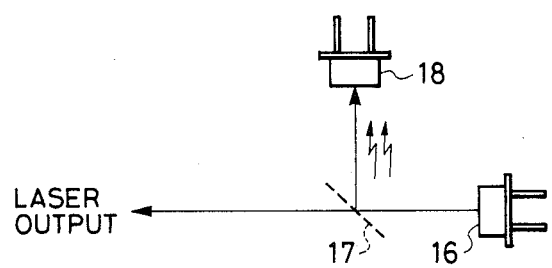
FIG. 5 is a drawing showing the method for monitoring the laser-output.
Figure 6:
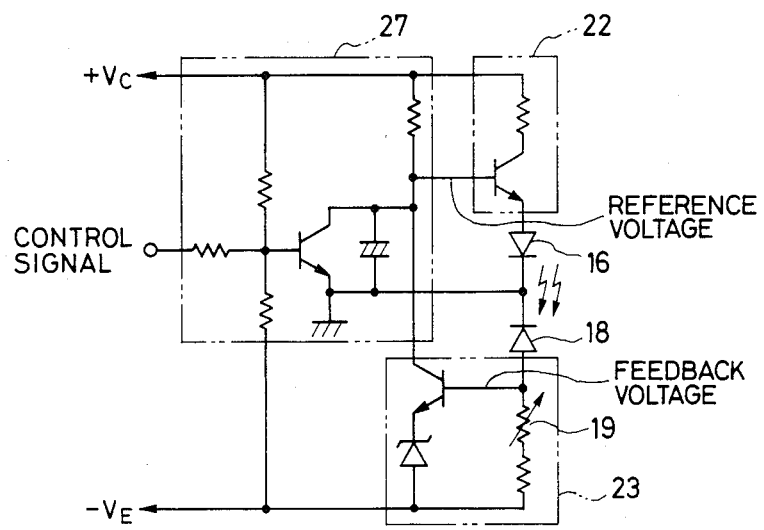
FIG. 6 is a diagram showing a semiconductor laser drive circuit.

Generally the laser-output intensity of the semiconductor laser easily changes according to ambient temperature change. In order that it is used as the laser beam source of the apparatus for detecting particles, it is required that the laser-output is constantly stable. In order to keep the laser-output constant for changes in temperature, it is a general practice, as shown in FIG. 5, to arrange a drive circuit to have functions that reflected laser-output of the semiconductor laser 16 by means of a half mirror 17 is detected by a monitoring sensor such as a photodiode 18 and fed back to the input voltage. An example of such drive circuits is shown in FIG. 6. In this circuit, the output current of the semiconductor laser 16 is controlled so that the output current of the photodiode 18 (that is, the laser-output of the semiconductor laser 16) may be kept constant any time. The setting of the laser-output is variable by a semifixed resistor 19.

Most of the latest semiconductor lasers are incorporated with a photodiode for monitoring the laser-output. In such case, the externally provided half mirror 17 and photodiode 18 in FIG. 5 are not required but the function in FIG. 6 can be provided by the use of the built-in monitoring photodiode. A dedicated IC to driving a semiconductor laser by means of feedback control is also available from the market.

Figure 7:
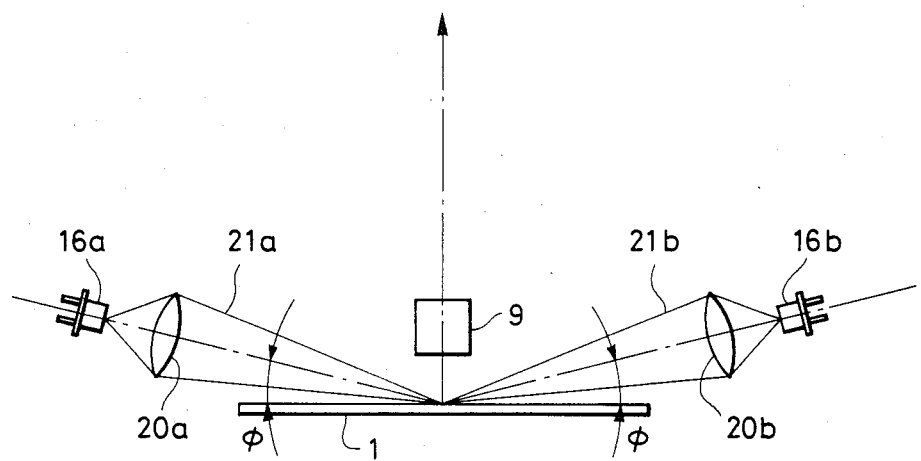
FIG. 7 is a drawing showing the method for using semiconductor lasers in the detecting for particles.

While the laser-output of the He-Ne laser is parallel light, the output of the semiconductor laser is somewhat diverged. Therefore, when the latter is used for illumination in the particle detection, it is necessary to use an collection lens 20 or the like as shown in FIG. 7 to converge the laser-output.

As described above, illumination by laser beams is effected from left and right sides to execute stable detection of anisotropic particles. In this case, since angles of inclination φ are equal for both the laser beams 21a, 21b from left and right sides, the laser beam from one of the opposing lasers (21b, for example) is reflected from the surface of the specimen 1 and enters into the other semiconductor laser (16a, for example). The intensity of the laser beam thus entering into the other laser is dependent on the surface conditions of the specimen 1 (roughness of the surface, density of the pattern, etc.). In the conventional method where a semiconductor laser 16 is provided with a photodiode 18 for monitoring the intensity of light incorporated therein, it monitors the laser-output from the opposite side as well as its own laser-output, so that it becomes impossible to execute the feedback control of the laser-output at a predetermined intensity during detection. That is, it has become to be known that the output intensity of the semiconductor laser 16 becomes different for each specimen 1 or, when the patterned specimen is applyed, the output of the semiconductor laser 16 changes even with the same specimen because the surface condition or density of the pattern differs from position to position on the same specimen 1.

Figure 8:
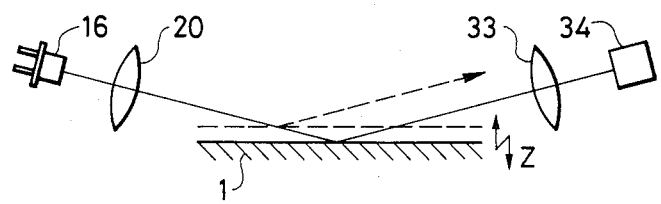
FIG. 8 is a drawing showing an embodiment of the method to measure the height of a specimen.

Such a method is also known as described in Japanese Patent Publication No. 57-53923 which allows a laser beam to be incident on the specimen at a predetermined angle and thereby detects the imaged position according to the position of the reflected light. Also in this case, a semiconductor laser can be used as the laser beam source as shown in FIG. 8. The laser-output of the semiconductor laser 16 is converged by a lens 20 and then applied onto the specimen 1. The laser beam reflected from the specimen 1 is converged by a converging lens 33 to be detected by a sensor 34. Since the position of the reflected light varies with the change of the position of the specimen in the vertical z direction, the position of the specimen can be measured by detecting the position of the reflected light by such as a position sensor 34. Since, at this time, a small quantity of reflected stray light from the surface of the sensor 34 (its glass window or the like) returns to the semiconductor laser 16 reversing through the same optical path to be detected by the monitoring photodiode. Also in this case, it has come to be known that the output of the semiconductor laser 16 shows a variation in the laser-output because the intensity of the returned beam varies with the surface condition of the specimen 1.

Now, a concrete embodiment of the present invention will be described.

Figure 1:
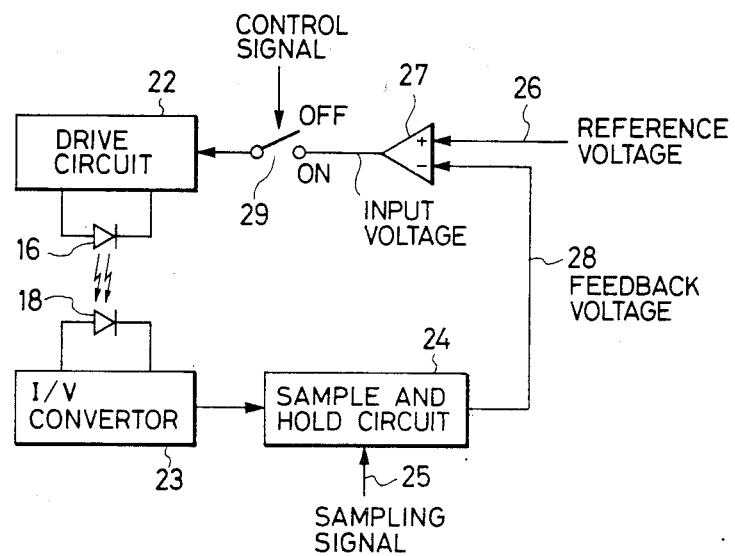
FIG. 1 is a diagram showing a hold circuit of the feedback voltage in an embodiment of the present invention.

FIG. 1 shows a circuit for holding a feedback voltage. A drive circuit 22 outputs a current proportional to an input voltage to the semiconductor laser 16 to light it on. The monitoring photodiode 18 receives a portion of the output light of the semiconductor laser 16 and outputs a current proportional to the intensity of the received light. A current-voltage converter circuit 23 converts the output current of the photodiode 18 into a voltage and supplies it to a sample and hold circuit 24. The sample and hold circuit 24 passes through the converted output when a sampling signal 25 is ON and holds the converted output when it is OFF. A differential amplifier 27 outputs a voltage proportional to the difference between the output 28 of the sample and hold circuit 24 and a reference voltage 26. A switch 29 switches ON/OFF the laser-output of the semiconductor laser.

By applying the above described circuits to each of the semiconductor lasers 16a and 16b of FIG. 7, a feedback control loop is formed when the sample signal 25 is ON, that is, the semiconductor laser 16 is driven so that the feedback voltage 28 of the sample and hold circuit 24 may become the same as the reference voltage 26. In this case even if the ambient temperature changes, the laser-output of the semiconductor laser 16 can be controlled to be constant. When the sampling signal 25 is OFF, the feedback voltage 28 just before it is turned OFF is held, and thereby, the semiconductor laser 16 is driven, then detection for particles is performed. By arranging such that the sampling signal 25 is turned ON at appropriate frequencies during a predetermined period of time, it becomes possible to keep the laser-output of the semiconductor laser 16 constant during the detection for particles.

Figure 2:
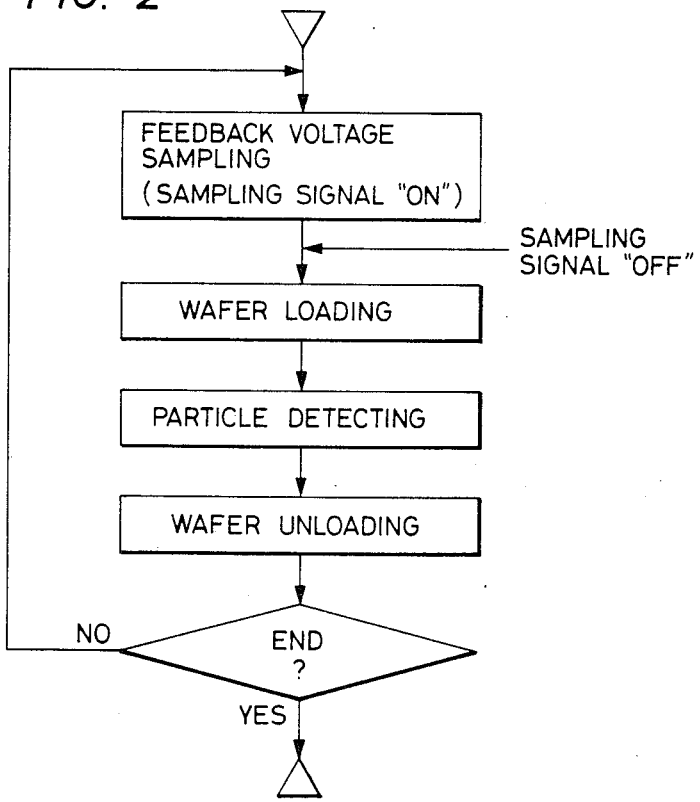
FIGS. 2 and 3 are charts showing flows in the detecting of wafers for particles thereon.

FIG. 2 shows a flow of a detecting process for particles, in which the loop of loading of the wafer, detecting for particles, and unloading of the wafer is normally repeated. That is, immediately before the detecting for particles, there always is a state of the detecting apparatus having no wafer set therein, in which the laser-output from the semiconductor laser on the other side does not enter into the monitoring photodiode on one side, so that the semiconductor laser on this side can have its own laser-output monitored. Accordingly, if the sampling signal is turned ON during the above period just before a wafer is loaded and the sampling signal is then held OFF throughout the period that the wafer is set in the apparatus, it becomes possible to stably keep the laser-output of the semiconductor laser at a predetermined intensity. The intensity of laser-output is predetermined by adjustment of REFERENCE VOLTAGE 26 (in FIG. 1) or adjustment of semi-fixed resistor 19 (FIG. 6). As described above, the period of time required for detecting for particles is at most several minutes, and the change of the ambient temperature during this period can be neglected, and therefore, the detecting for particles at a constant laser-output of the semiconductor laser is enabled.

Figure 3:
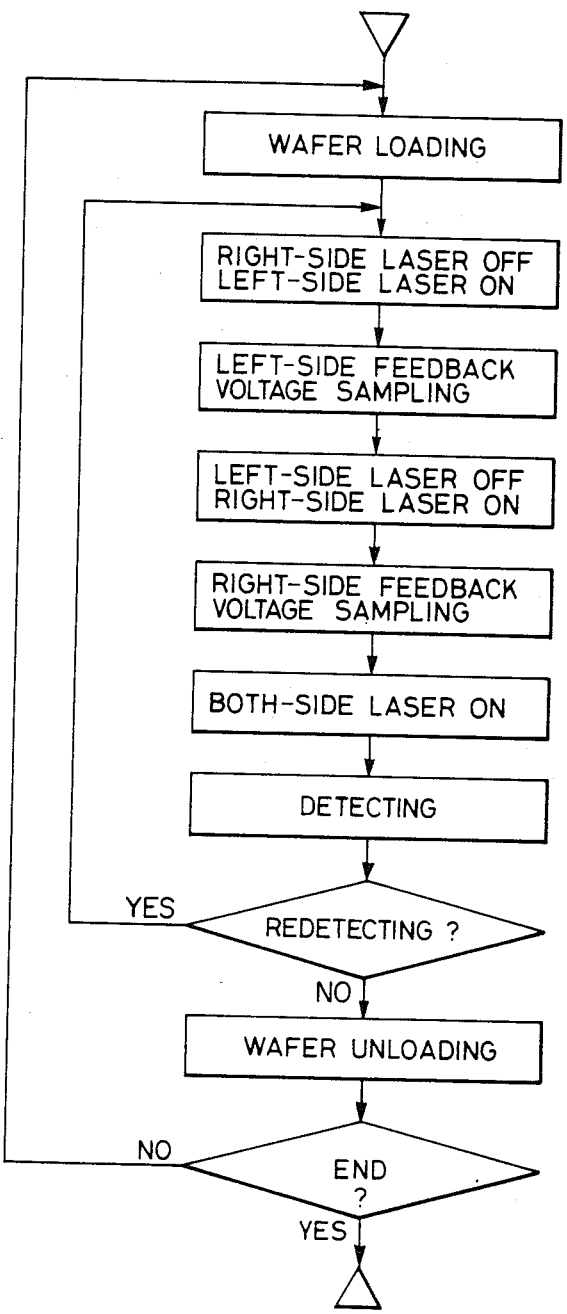

Sometimes, after one detecting process for particles has been finished, the next detecting process for particles is started without unloading a wafer. An example is shown in FIG. 3 where the same wafer is tested many times in order to ensure repeatable performance of the apparatus. In this case, the switch 29 shown in FIG. 1 is used just before the detection. First, the semiconductor laser 16a on the left side is turned ON, while the semiconductor laser 16b on the right side is turned OFF, and the sampling signal for the left side is turned ON. Thereafter, the semiconductor laser 16b on the right side is turned ON, while the semiconductor laser 16a on the left side is turned OFF, and the sampling signal for the right side is turned ON. Since the feedback voltages are held for their respective semiconductor lasers, the laser-outputs can then be stably kept at the predetermined intensity by turning ON the semiconductor lasers on both sides even if the wafer remains set in the apparatus.

Figure 9:
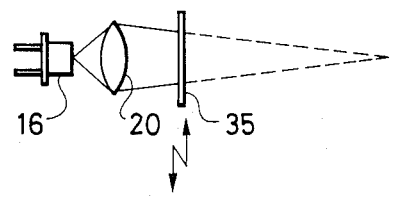
FIG. 9 is a drawing showing an embodiment of cutting off laser-output by the use of a shutter.
Figure 10:
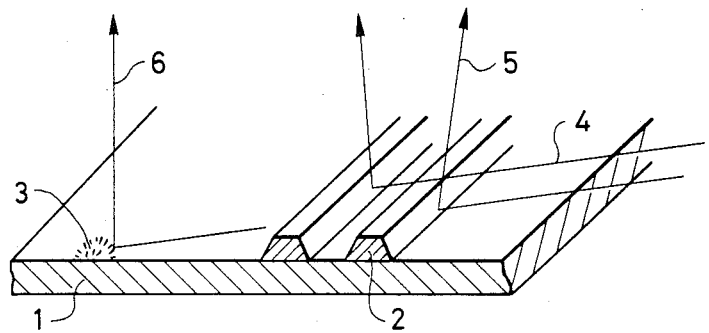
FIGS. 10 to 12 are drawings for explaining a prior art device.
Figure 11A:
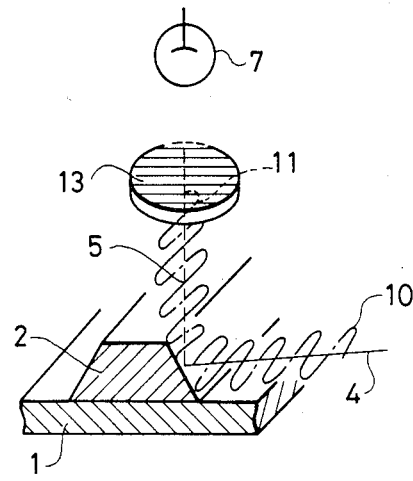
Figure 11B:
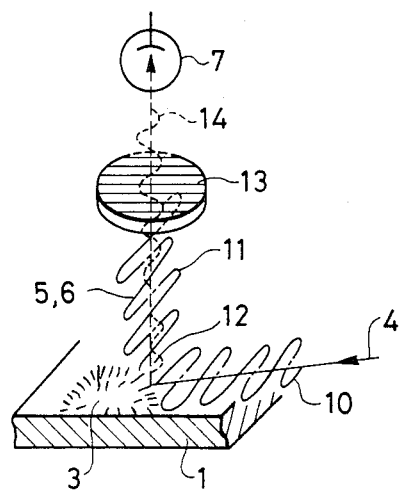
Figure 12:
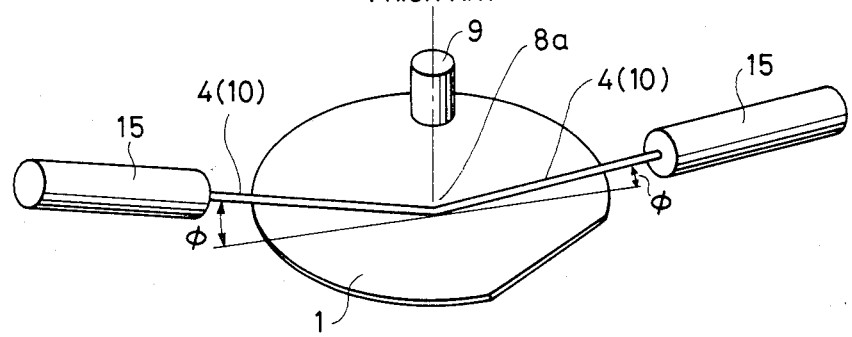

If a shutter 35 is inserted for cut the laser-output at shown in FIG. 9, then the laser-output from the opposing semiconductor laser (FIG. 7) or returned stray light reflected from the sensor (FIG. 8) is prevented from getting therein, and so, by arranging such that the sampling signal is turned ON with the shutter 35 inserted and the shutter is removed from the optical path during the course of detecting or measuring, similar performance to that described above is achieved.

Figure 4:
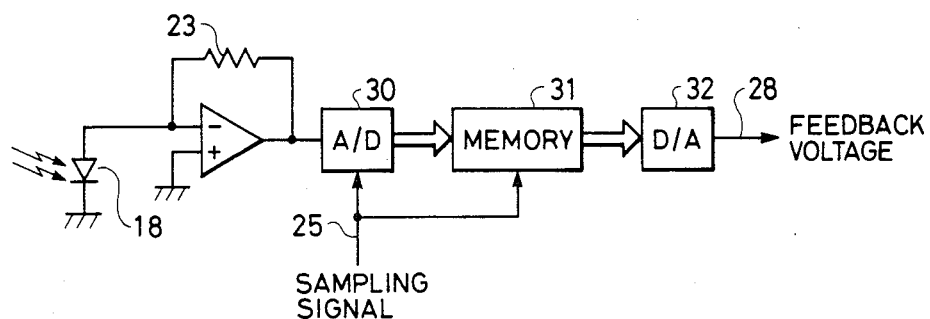
FIG. 4 is a diagram showing a sample hold circuit according to the present invention.

If the sample and hold circuit 24 is arranged in an analog circuit, attenuation of the held voltage becomes a problem when the holding time period is long. In the case of detecting for particles, since the holding time becomes as long as several minutes, it is preferable that a digital sample and hold circuit as shown in FIG. 4 is employed. Denoted by 23 in FIG. 6 is a current-voltage converter circuit for outputting the voltage proportional to the output of the monitoring current from photodiode 18. Denoted by 30 in FIG. 4 is an analog-to-digital converter for converting the analog output of the current-voltage converter circuit 23 into a digitized signal when the sampling signal is turned ON. The converted digitized signal is stored in a memory 31, and the stored signals in the memory 31 are adapted to be constantly converted into an analog signal by the digital-to-analog converter 32, and thus, a sample and hold circuit free from the attenuation is provided.

As described so far, it has been arranged such that feedback control of one semiconductor laser is performed just before the start of detection of particles, with the laser-output from the opposing semiconductor laser arranged not to enter into the semiconductor laser, according to the output of its monitoring photodiode to control the semiconductor laser to emit the laser-output of the same intensity as a predetermined intensity and such that the feedback voltage is held unchanged during the detecting process, and thereby, it has been made possible to stably keep the laser-output unaffected by the opposing semiconductor laser. Although description has so far been made on detecting for particles on a wafer, the same arrangement is applicable to that on a photomask, magnetic bubble wafer and etcs.

According to the present invention as described in the foregoing, the laser-output of the semiconductor laser can be kept stable during a detecting process, and therefore, the effect is obtained that a uniform intensity illumination performance for detecting particles can be maintained even if different specimens are detected.

What is claimed is:

1. Apparatus for detecting particles on a specimen surface during a detecting period comprising:

means for illuminating a specimen surface including a pair of semiconductor lasers and associated optical elements disposed at an angle of inclination relative to said surface and on opposite sides of said specimen surface to oppose each other so that the laser beams from each of said semiconductor lasers are focused onto the specimen surface in a manner that some illumination from each laser is reflected from the specimen surface and thereby directed to the opposed laser; and means stably maintaining illumination from each semiconductor laser at a predetermined intensity during said detecting period when both lasers are simultaneously illuminating said surface comprising:

a pair of sensors (18a, 18b) for detecting the output illumination for a respective one of the semiconductor lasers (16a, 16b);

a pair of current-voltage converter circuits (23a, 23b) for converting the output current of each of the sensors into a separate output voltage;

a pair of sample and hold circuits (24a, 24b) for sampling and holding the converted output voltage by a sampling signal (25) being inputted during the period just prior to initiation of said determining period;

a pair of differential amplifiers (27a, 27b) each outputting a separate voltage proportional to a difference between an output signal (28) of each of the sample and hole circuits (24a, 24b) and a reference voltage (26); and a pair of semiconductor laser drive circuits (22a, 22b) each responsive to the output voltage from the respective differential amplifiers (27a, 27b) for controlling each of said semiconductor lasers to have a predetermined intensity during said detecting period.

2. Apparatus according to claim 1 further comprising:
   shutter means associated with each of said semiconductor lasers; and means for actuating a shutter means associated with one laser while the other laser output is monitored by the sensor associated therewith to establish sequentially for each laser the level of voltage to be applied to the drive circuit associated with the respective semiconductor laser beam during the period of detection when the specimen surface is being illuminated simultaneously by beams from both lasers.

3. Apparatus according to claim 1 wherein said illuminating means further includes switching means for individually turning each of the pair of semiconductor lasers on or off;

means whereby one semiconductor laser is turned on and the other semiconductor laser is turned off to establish the level of voltage to be applied to said one laser;

means whereby the other semiconductor laser is turned on and said one semiconductor laser is turned off to establish the level of voltage to be applied to said other laser; and means applying the established voltage level to the respective drive circuits for each semiconductor laser during said detecting period.

4. Apparatus according to claim 3 further including means for polarizing each of the laser beams.

5. Apparatus as defined in claim 4 further including a detecting means including an analyzer for detecting non-polarized light scattered from a pattern on the specimen surface.

* * * * *